US 6,749,303 B2

(12) United States Patent
Fukuma et al.

(10) Patent No.: US 6,749,303 B2
(45) Date of Patent: Jun. 15, 2004

(54) OPTOMETRY APPARATUS AND DIFFRACTION GRATING PLATE USED IN THE SAME

(75) Inventors: Yasufumi Fukuma, Tokyo (JP); Yasuo Kato, Tokyo (JP); Makoto Fujino, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 107 days.

(21) Appl. No.: 10/125,907

(22) Filed: Apr. 19, 2002

(65) Prior Publication Data

US 2002/0167641 A1 Nov. 14, 2002

(30) Foreign Application Priority Data

Apr. 20, 2001 (JP) ........................................ 2001-123245

(51) Int. Cl.⁷ ................................................ A61B 3/02
(52) U.S. Cl. ...................................................... 351/233
(58) Field of Search ............................... 351/205, 211, 351/214, 216, 212, 233, 236, 246; 359/482, 618, 619, 621, 622

(56) References Cited

U.S. PATENT DOCUMENTS 3,880,502 A * 4/1975 Humphrey .................. 351/246
5,619,373 A * 4/1997 Meyerhofer et al. ......... 359/482
5,748,375 A * 5/1998 Yamana ....................... 359/622
5,835,190 A * 11/1998 Miyake ........................ 351/212
5,914,772 A 6/1999 Dyer

FOREIGN PATENT DOCUMENTS

GB 865361 4/1961

OTHER PUBLICATIONS

Lu et al., "The Fabrication of a 25×25 Multiple Beam Splitter," *Optics Communications* 72 (1989) 15, Jul. No. 3/4.

Singh, "Diffraction Gratings: Aberrations and Applications," *Optics & Laser Technology* 31 (1999) 195–218.

* cited by examiner

*Primary Examiner*—George Manuel
(74) *Attorney, Agent, or Firm*—Chapman and Cutler LLP

(57) ABSTRACT

An optometry apparatus of the present invention comprises an optical element 26 provided in a correction optical system 1, which has a spherical lens 24 and a cylindrical lens 25 and which corrects examined eyes E to be subjected to optometry, wherein the optical element is used so that targets are seen as if they were dispersed in a plane orthogonal to an optical axis O1 and shown simultaneously at a different distance or position in a direction of an optical axis through the eyes E to be subjected to optometry.

16 Claims, 18 Drawing Sheets

OPTOMETRY APPARATUS AND DIFFRACTION GRATING PLATE USED IN THE SAME

BACKGROUND OF THE INVENTION

The present invention relates to an optometry apparatus having an optical element by which targets can be seen as if they were dispersed in a plane orthogonal to an optical axis and presented simultaneously at a different distance or position in a direction of an optical axis through examined eyes to be subjected to optometry, and a diffraction grating plate as an optical element used in the same.

Conventionally, an optometry apparatus makes a precise decision of an astigmatic axis of examined eyes to be subjected to optometry and of an astigmatic degree by use of a cross cylinder lens. As a method for deciding the astigmatic axis and astigmatic degree precisely using this cross cylinder lens, a cross cylinder method and an auto-cross cylinder method are known.

In any method, firstly a spherical degree S, a cylindrical degree C, and an axial angle A of a cylindrical axis O are roughly measured, thereafter, the astigmatic axis of the examined eyes to be subjected to optometry and the astigmatic degree are precisely measured.

For example, it is assumed that a spherical degree S (=−1.00D), a cylindrical degree C (=−0.50D) and an axial angle A of a cylindrical axis O (=90 degree) are set as a result of the optical characteristic of one lens of eyeglasses in use currently by a lens meter.

At the time of optometry, first of all, in order to remove accommodation power of eyes, as shown in FIG. 1, a spherical lens 2 whose the spherical degree S is, for example, +3.00D, which is higher than a prospective degree, is set to an optometric window of a correction optical system 1 by fogging, and an eyesight-test chart is shown to a subject. In the case of the spherical degree S (=−1.00D), the spherical lens 2 with the spherical degree S (=+2.00D) is set to the optometric window, and the spherical degree S of the spherical lens 2 to be set to the optometric window is reduced by −0.25D so as to increase eyesight.

Then, an astigmatic test chart 3 illustrated in FIG. 2 is shown to the subject at the stage which is one step before desirable eyesight, and the subject is asked how the astigmatic test chart 3 is seen.

In a case where the astigmatic test chart 3 is blurredly seen uniformly, it can be judged that the subject is not a person with astigmatism. Here, it is assumed that the subject is a person with astigmatism. For example, if an answer "I can see the direction at 3 o'clock clearly" is received in response to a question "which direction at a clockwise can you see?", a cylindrical lens 4 is set to the optometric window of the correction optical system 1 and the cylindrical axis O is set in a direction orthogonal to a direction where clear vision can be obtained. Namely, the axial angle A of cylindrical axis O is set to 90 degrees.

After that, the cylindrical degree C of the cylindrical lens 4 to be set to the optometric window is increased 0.25 by 0.25, and the approximate measurement is completed when the degree of the cylindrical lens 4 reaches a value where the astigmatic test chart 3 is clearly seen uniformly.

Additionally, in FIG. 1, reference numeral O1 denotes an optical axis of the correction optical system 1.

Next, precise measurement of the cylindrical axis O and cylindrical degree C is performed.

In case of the cross cylinder method, a cross cylindrical lens 5 is inserted in the correction optical system 1. This cross cylinder lens 5 is structured such that the axis of (−) axial cylindrical lens is orthogonal to that of (+) axial cylindrical lens as shown in FIG. 1.

Then, an intermediate axis 6 of the cross cylindrical lens 5 is allowed to conform to the cylindrical axis O of the cylindrical lens 4. Next, the cross cylindrical lens 5 is reversed using the intermediate axis 6 of the cross cylindrical lens 5 as a central axis. Then, the subject is allowed to look at a point group chart 7 of FIG. 3.

Before and after the cross cylindrical lens 5 is reversed at the time of showing this point group chart 7, the cylindrical lens 4 and cross cylindrical lens 5 are integrally rotated in a direction where a clear view is obtained by, for example 5 degrees to measure the axial angle A of the cylindrical lens 4 precisely.

Sequentially, as illustrated in FIG. 4, any one of (+) axis and (−) axis of the cross cylindrical lens 5 is confirmed to the cylindrical axis O of the cylindrical lens 4. FIG. 4 shows a state in which (+) is confined to the cylindrical axis O. Then, the point group chart of FIG. 3 is shown to the subject. Next, the cross cylinder lens 5 is reversed using the intermediate axis 6 as a central axis and the (−) axis is conformed to the cylindrical axis O. Then, the point group chart of FIG. 3 is shown to the subject. After asking the subject a question about which way the chart can be clearly seen before or after the cross cylindrical lens 5 is reversed, the cylindrical degree C of the cylindrical lens 2 is set to a direction where a clear view can be obtained.

Thus, precise measurement of the subject's astigmatic axis and astigmatic degree is completed.

In case of the auto-cross cylinder method, an auto cross cylindrical lens 8 shown in FIG. 5 is used. This auto cross cylindrical lens 8 includes a triangular prism 9 and cross cylindrical lenses 10, 11. The cross cylindrical lenses 10 and 11 have the degree of, for example, ±0.25D or ±0.5D, and plus and minus axes of the cross cylindrical lenses 10 and 11 are orthogonal with respect to each other.

The precise measurement of the astigmatic axis and astigmatic degree using this auto cross cylindrical lens 8 is carried out, for example, as follows:

The approximate measurement of the spherical degree S, cylindrical degree C, and axial angle A of cylindrical axis O is the same as the case of the cross cylinder method.

After the approximate measurement of the spherical degree S, cylindrical degree C, and axial angle A of cylindrical axis O, an intermediate axis 12 of the auto cross cylindrical lens 8 is conformed to the cylindrical axis O of the cylindrical lens 4 as shown in FIG. 6. Consequently, the plus axis (+) of the upper-side cross cylinder lens 10 is set to a direction at 45 degrees with respect to the cylindrical axis O and the minus axis (−) thereof is set to a direction at 135 degrees. Moreover, the minus axis (−) of the lower-side cross cylinder lens 11 is set to a direction at 45 degrees with respect to the cylindrical axis O and the plus (+) thereof is set to a direction at 135 degrees.

Then, the point group chart 7 of FIG. 3 is similarly shown to the subject so that the subject is allowed to perform comparison between the point group chart 7 seen through the upper-side cross cylinder lens 10 and the point group chart 7 seen through the lower-side cross cylinder lens 11 simultaneously to check which chart can be clearly seen. Then, the cylindrical lens 4 is rotated integrally with the auto cross cylinder 8 in the direction where a good view can be obtained. Thus, the axial angle A of the cylindrical axis O is decided.

After that, the cross cylinder lenses 10 and 11 are rotated so that the plus axis (+) of the cross cylinder lens 10 is conformed to the cylindrical axis O and the minus (−) of the cross cylinder lens 11 is conformed to the cylindrical axis O as illustrated in FIG. 7. After performing comparison between the point group chart 7 seen through the cross cylinder lens 10 and the point group chart 7 seen through the cross cylinder lens 11 simultaneously to check which chart can be clearly seen, the cylindrical degree C of the cylindrical lens 4, which is inserted in the optical path of the correction optical system 1, is changed to the direction where the good view can be obtained.

Thus, precise measurement of the axial angle A of the cylindrical axis and cylindrical degree C is completed.

Next, precise measurement of the spherical degree S is performed.

In this precise measurement of the spherical degree S, a so-called red and green chart 13 is shown as illustrated in FIG. 8. In a case where a target seen through a red filter can be seen well, since such a situation is considered that correction is lack, the spherical degree S of the spherical lens 2 is increased. In a case where a target seen through a green filter can be seen well, since such a situation is considered that correction is excessive, the spherical degree S of the spherical lens 2 is decreased.

Thus, the precise measurement of the spherical degree S is completed.

However, in the optometry apparatus by the cross cylinder method, since an operation to reverse the cross cylinder lens 5 is carried out at the target comparing time, the targets cannot be compared simultaneously. Accordingly, since judgment is made by separated observation in which judgment is made with a time difference, it is difficult for the subject to judge which the target can be seen well.

Moreover, there is a disadvantage in which the spherical degree S, cylindrical degree C and the axial angle A of the cylindrical axis cannot be measured simultaneously, Still moreover, many subjects answer that the subject can see the respective points 7*a* more easily whose profile lines 7*b* are clearly seen in the direction of astigmatic axis as illustrated in a partially enlarged view of FIG. 9, as compared with the respective points 7*a* of the point group chart 7 of FIG. 3 which are blurredly seen uniformly.

On the other hand, in the optometry apparatus by the auto cross cylinder method, since a contrastive observation that performs comparison between the targets simultaneously is performed, the subject can easily judge which the target can be seen well as compared with the case of using the cross cylinder method.

However, similarly to the cross cylinder method, this auto cross cylinder method has a disadvantage in which the spherical degree S, cylindrical degree C and axial angle A of cylindrical axis cannot be measured simultaneously. Moreover, similar to the cross cylinder method, many subjects answer that the subject can see more easily the respective points 7*a* whose profile lines 7*b* are clearly seen in the direction of astigmatic axis as illustrated in a partially enlarged view of FIG. 9, as compared with the respective points 7*a* of point group chart 7 of FIG. 3 which are blurredly seen uniformly.

Still moreover, though the contrastive observation that contrasts the targets simultaneously and compares them can be carried out, the number of targets to be compared is only two and it is difficult to judge which is clearly seen.

In addition, in a case where the subject is extremely farsighted or nearsighted, a difference occurs in the way to see the targets simultaneously presented due to influence of aberration of the correction optical system 1 unless the eyes to be subjected to optometry are set to a correct position.

In the case of precise measurement of spherical degree using the red and green test chart 13, there are many answers indicating that the target with a favorite color is seen well.

The present invention has been made with consideration given to the aforementioned problems, and it is an object of the present invention is to provide an optometry apparatus that can measure a spherical degree S, a cylindrical degree C and an axial angle A of a cylindrical axis O at one time, so that targets are seen as if they were disposed in a plane orthogonal to an optical axis and shown simultaneously at a different distance or position in a direction of the optical axis.

SUMMARY OF THE INVENTION

An optometry apparatus according to the present invention comprises an optical element constructed so that targets appear to examined eyes to be subjected to optometry as if the targets were dispersed on a plane orthogonal to an optical axis and shown simultaneously at a different distance or position in a direction of the optical axis.

In an optometry apparatus according to the present invention, the optical element is formed of a diffraction grating plate where periodicity of a diffraction grating changes.

An optometry apparatus according to the present invention comprises an optical element in a correction optical system which has a spherical lens and a cylindrical lens and corrects eyes to be subjected to optometry, the optical element being constructed such that targets appears to the eyes as if the targets were dispersed in a plane orthogonal to an optical axis and shown simultaneously at a different distance or position in a direction of the optical axis.

In the optometry apparatus according to the present invention, the optical element is capable of going/coming to/from an optical path of the correction optical system.

In the optometry apparatus according to the present invention, then optical element is formed of a diffraction grating plate where periodicity of a diffraction grating changes.

In the optometry apparatus according to the present invention, when the diffraction grating plate is inserted in an optical axis of the correction optical system, the targets are shown by a single-color light source.

In the optometry apparatus according to the present invention, when the diffraction grating plate is inserted in the optical axis of said correction optical system, a light quantity of the single-color light source is increased.

In the optometry apparatus according to the present invention, a subject himself/herself designates a target, which seems to be the best among the plurality of targets shown simultaneously and adjusts said correction optical system.

In the optometry apparatus according to the present invention, matrix signs, which can designate the plurality of targets in the form of matrix, are simultaneously shown to the eyes to be subjected to optometry such that the subject himself/herself is caused to designate the target, which seems to be the best among the plurality of targets shown simultaneously.

In the optometry apparatus according to the present invention, the matrix signs are shown in an optical path of the correction optical system through a half mirror.

In the optometry apparatus according to the present invention, the matrix signs are shown with a wavelength by which no diffraction power is generated.

In the optometry apparatus according to the present invention, the subject himself/herself adjusts the correction optical system using a joystick such an target, which seems to be the best among the plurality of targets shown simultaneously, is positioned on an optical axis of the correction optical system.

In the optometry apparatus according to the present invention, the diffraction grating plate is rotated together with the cylindrical lens, so that a spherical degree, a cylindrical degree and an axial angle of a cylindrical axis are precisely measured.

In the optometry apparatus according to the present invention, the diffraction grating plate is rotated by 45 degrees from an initial setting state to determines a spherical degree, a cylindrical degree and an axial angle of a cylindrical axis by calculation. A spherical degree, a cylindrical degree and an axial angle of a cylindrical are determined by calculation where the spherical degree, the cylindrical degree and the axial angle of cylindrical axis determined by the calculation are synthesized with a cylindrical degree and an axial angle of a cylindrical axis determined by approximate measurement. The spherical degree, the cylindrical degree and the axial angle of cylindrical axis are precisely measured by the synthesized spherical degree, cylindrical degree, and axial angle of cylindrical axis obtained by this calculation.

In the optometry apparatus according to the present invention, the diffraction grating plate is rotated by 60 degrees two times from an initial setting state to determine a spherical degree, a cylindrical degree and an axial angle of a cylindrical by calculation. A spherical degree, a cylindrical degree and an axial angle of a cylindrical axis are determined by calculation where the spherical degree, the cylindrical degree and the axial angle of cylindrical determined by the calculation are synthesized with a spherical degree, a cylindrical degree and an axial angle of a cylindrical axis determined by approximate measurement. The spherical degree, the cylindrical degree and the axial angle of cylindrical axis are precisely measured by the synthesized spherical degree, cylindrical degree, and axial angle of cylindrical axis determined by this calculation.

A diffraction grating plate according to the present invention constructed such that targets appear to eyes to be as if the targets were dispersed in a plane orthogonal to an optical axis and shown simultaneously at a different distance or position in a direction of an optical axis through eyes to be subjected to optometry.

DETAILED DESCRIPTION OF THE PREFERRED EMBODIMENTS

Figure 1:
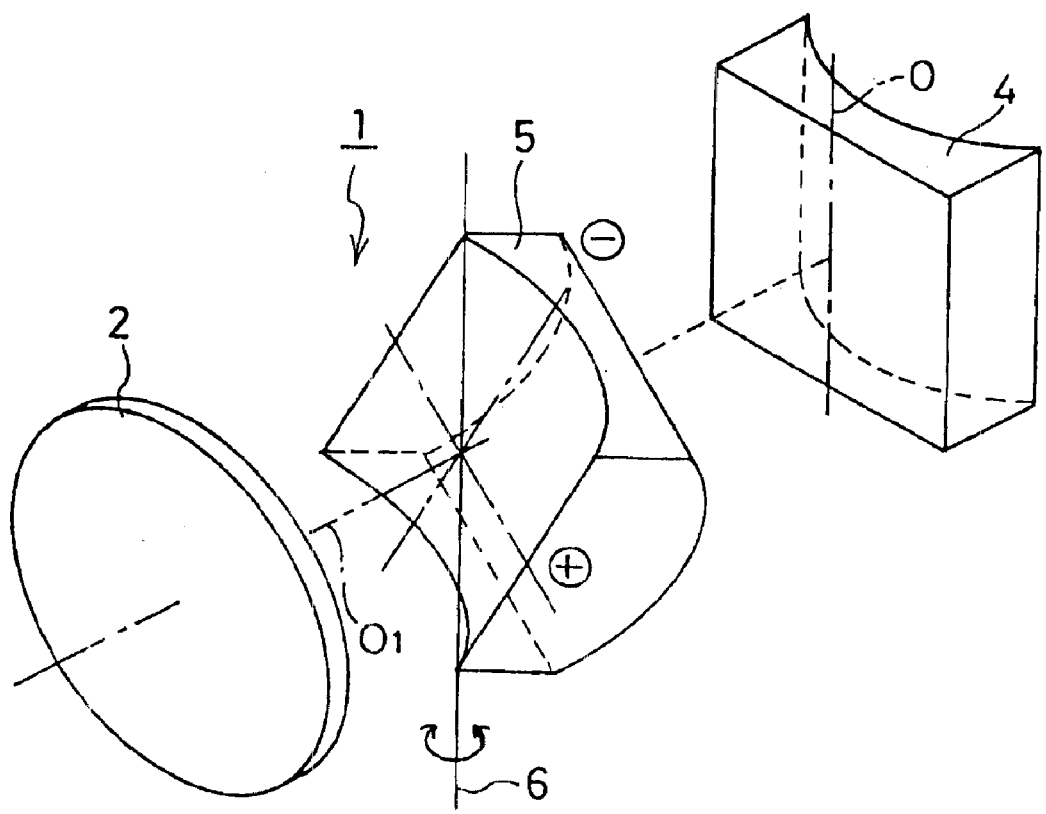
FIG. 1 is an explanatory view illustrating an example of precise measurement of an axial angle of a cylindrical axis of a cylindrical lens by a cross cylinder method.
Figure 2:
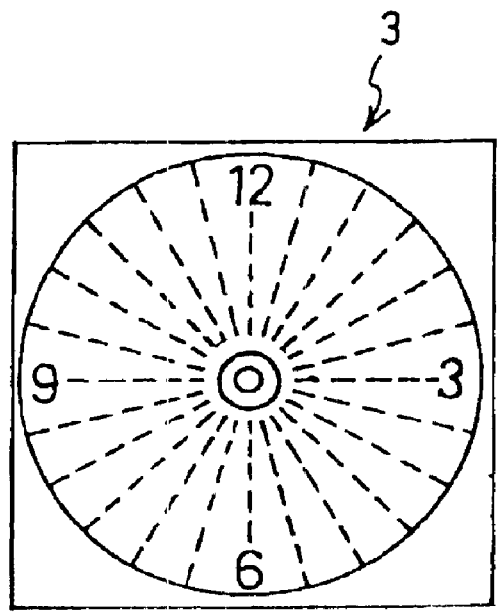
FIG. 2 is a view illustrating one example of an astigmatic chart.
Figure 3:
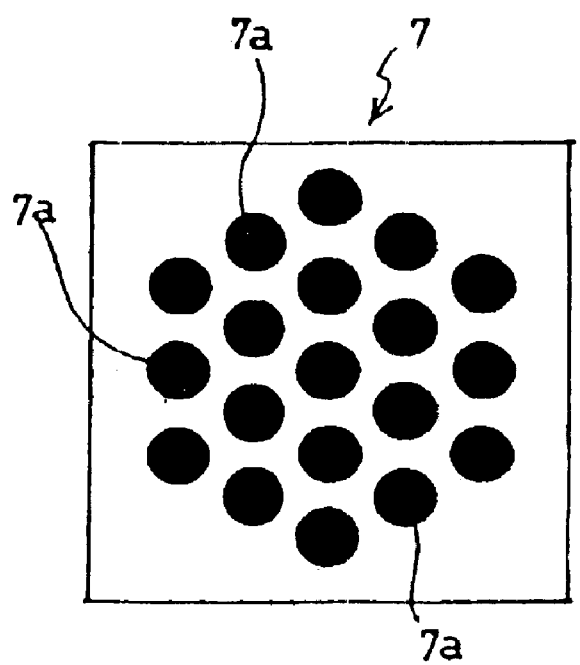
FIG. 3 is a view illustrating one example of point group targets.
Figure 4:
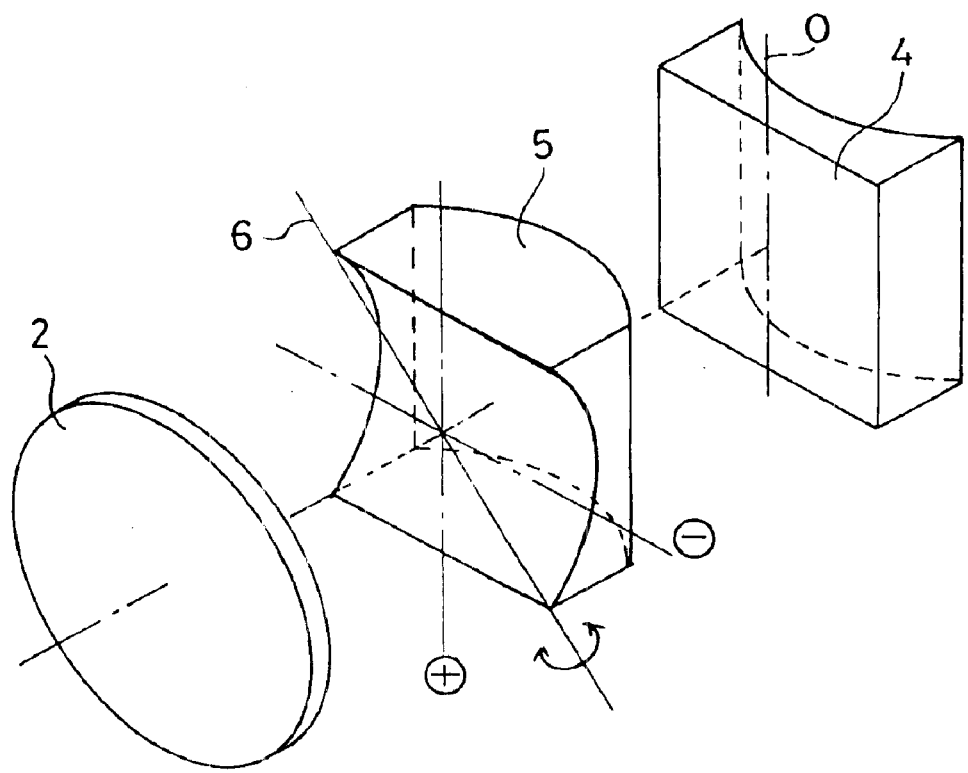
FIG. 4 is a view illustrating one example of precise measurement of a cylindrical degree of a cylindrical lens by the cross cylinder method.
Figure 5:
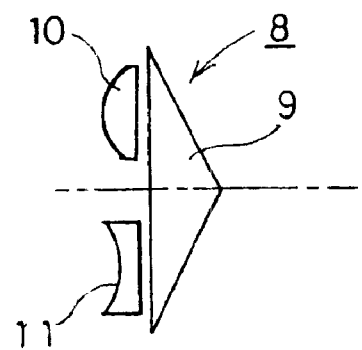
FIG. 5 is a side view showing one example of an auto cross cylinder.
Figure 6:
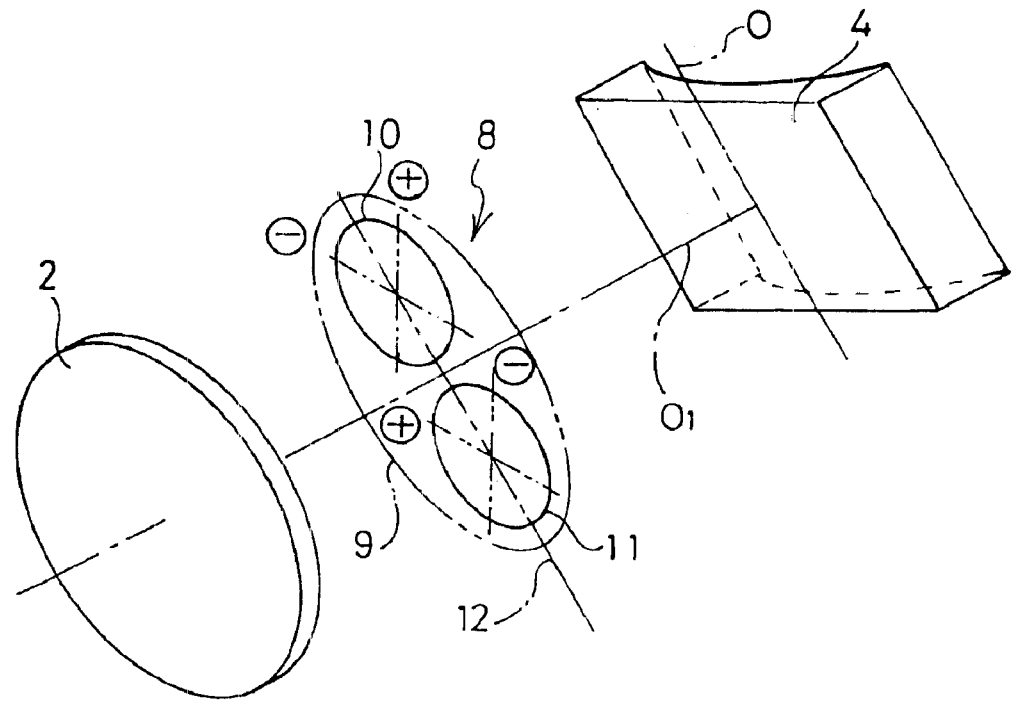
FIG. 6 is an explanatory view illustrating one example of precise measurement of an axial angle of a cylindrical axis of a cylindrical lens by an auto cross cylinder method.
Figure 7:
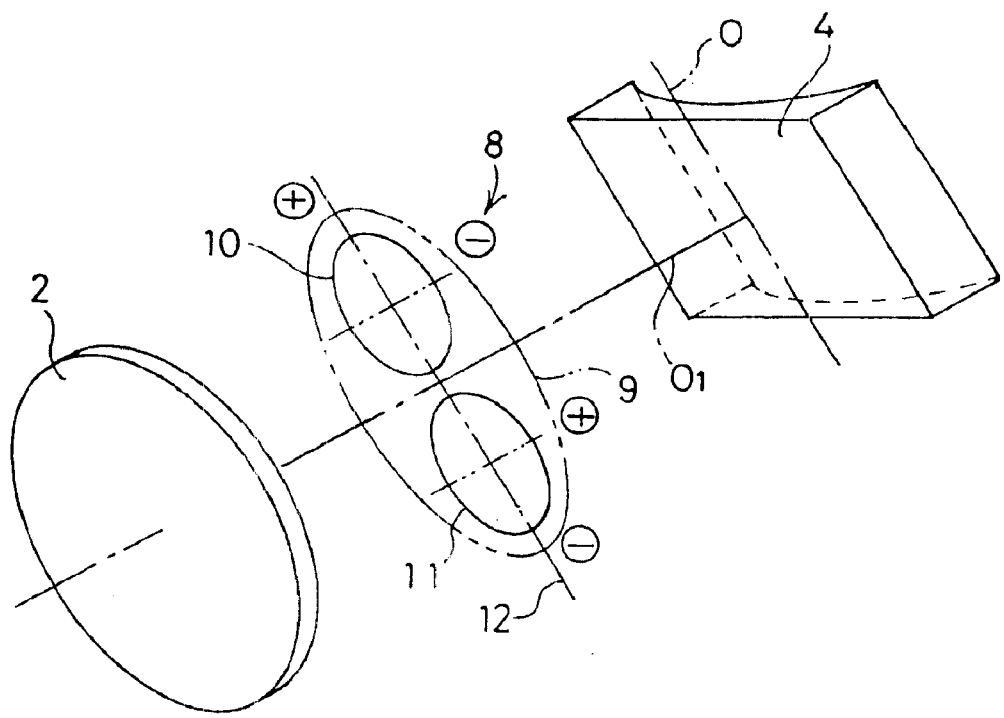
FIG. 7 is an explanatory view illustrating an example of precise measurement of a cylindrical degree of a cylindrical lens by an auto cross cylinder method.
Figure 8:
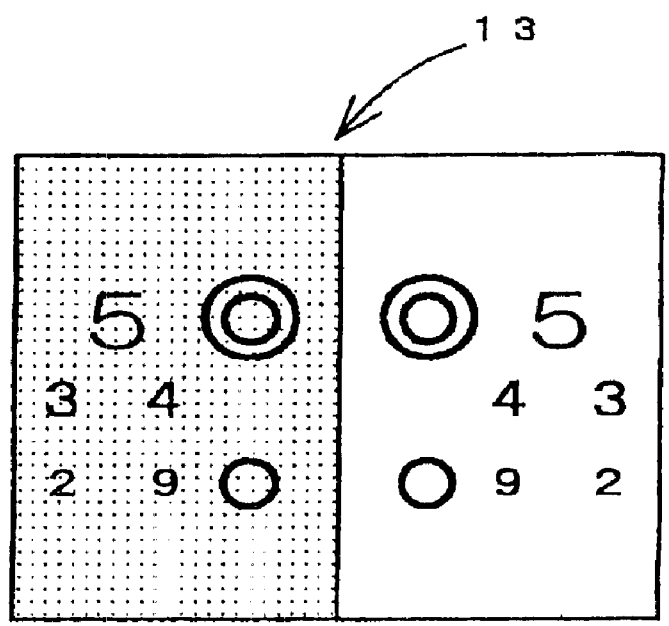
FIG. 8 is a view illustrating one example of a red and green chart.
Figure 9:
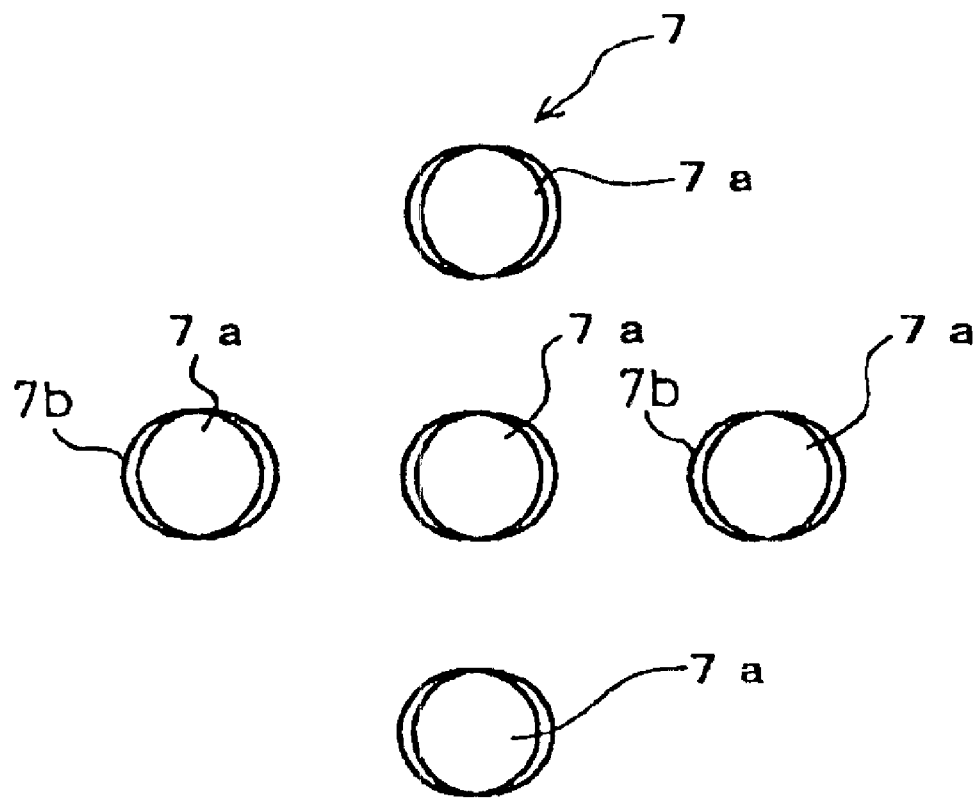
FIG. 9 is an explanatory view illustrating one way how a point group of FIG. 3 is seen.
Figure 10:
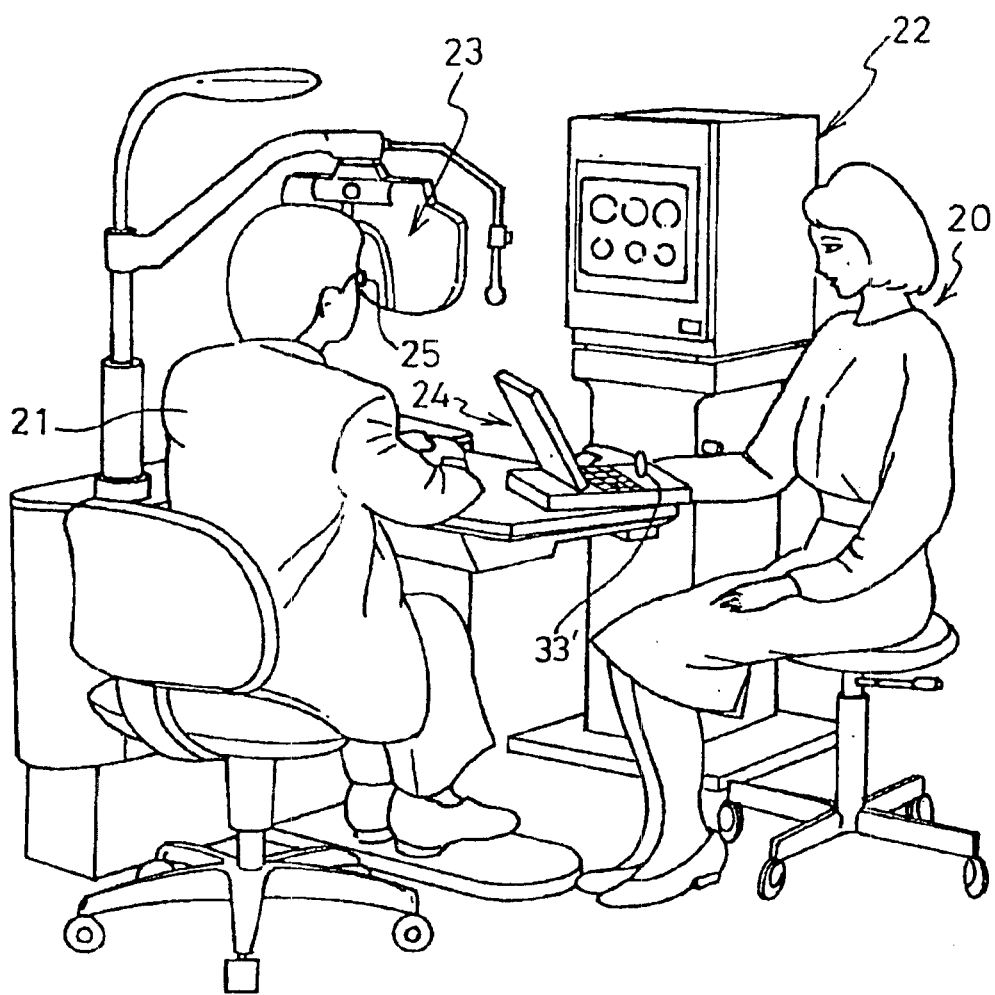
FIG. 10 is an outline view showing a general outline of an optometry apparatus according to the present invention.

FIG. 10 is an explanatory view showing a schematic structure of an optometry apparatus according to the present invention.

In FIG. 10, reference numeral 20 is an examiner, 21 is a subject, 22 is a target presenting apparatus, 23 is a Phoroptor, and 24 is a controller.

Figure 11:
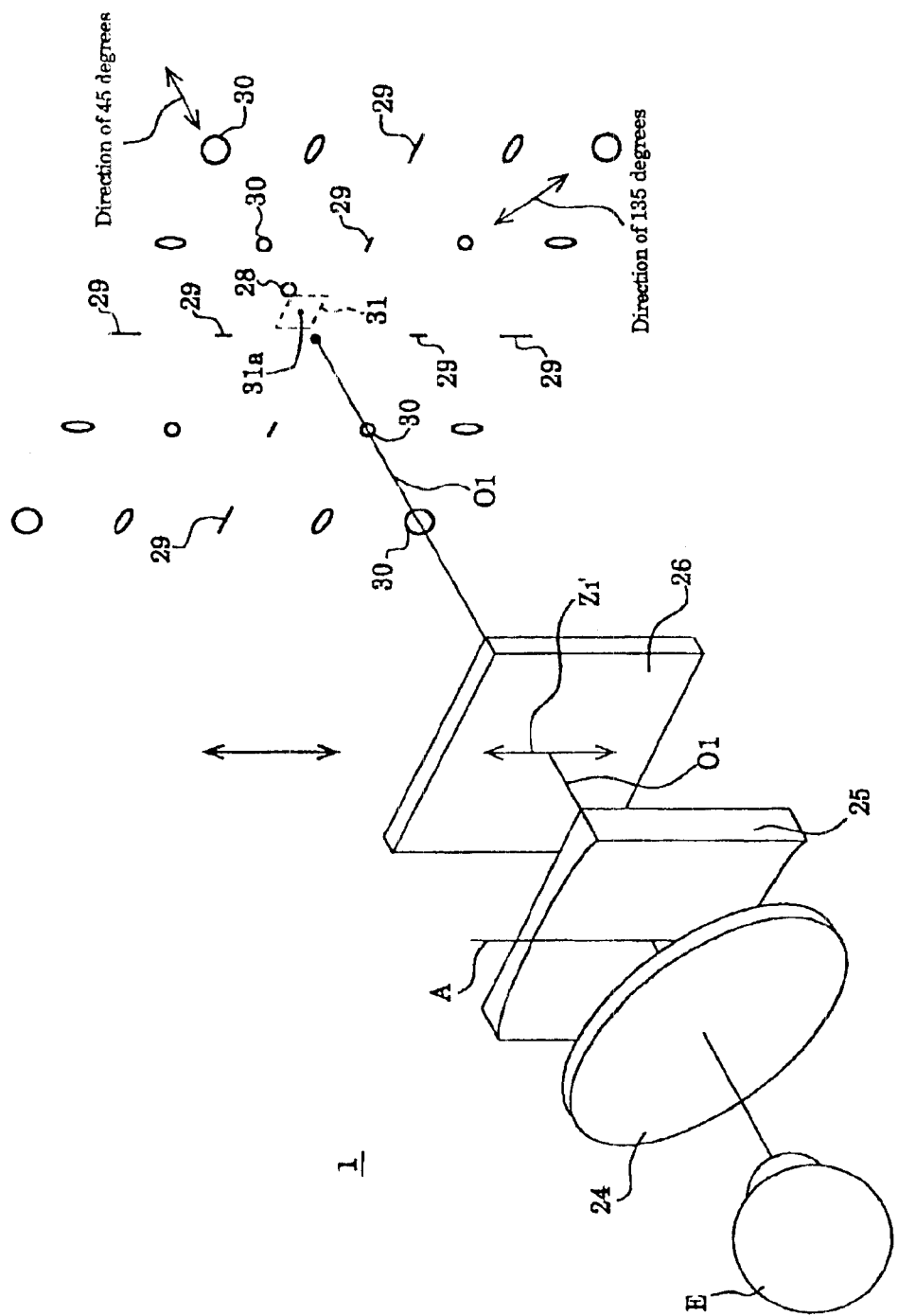
FIG. 11 is an explanatory view showing a general outline of a correction optical system according to the present invention.

The Phoroptor 23 is provided with a spherical lens 24 having a different spherical degree S, a cylindrical lens 25 having a different cylindrical degree C and a diffraction grating plate 26 as an optical element as shown in FIG. 11. These spherical lens 24, cylindrical lens 25 and diffraction grating plate 26 are set to an optometric window of the Phoroptor 23 as required.

FIG. 11 shows a state in which approximate measurement of a spherical degree S, a cylindrical degree C and an axial angle A with respect to examined eyes E subjected to optometry is finished and the spherical lens 24 and the cylindrical lens 25, which serve as correction optical system 1, are inserted in the optometry window. Here, it is assumed that the axial angle A of the cylindrical axis O of the cylindrical lens 25 is set to 90 degrees similar to the conventional case.

The diffraction grating plate 26 is used to carry out precise measurement of an astigmatic axis of the eyes to be subjected to optometry, an astigmatic degree, and a spherical degree. The diffraction grating plate 26 is inserted in the optical path of the correction optical system 1 in place of the conventional cross cylindrical lens, and is capable of going/coming to/from the optical path of the correction optical system 1.

Figure 12:
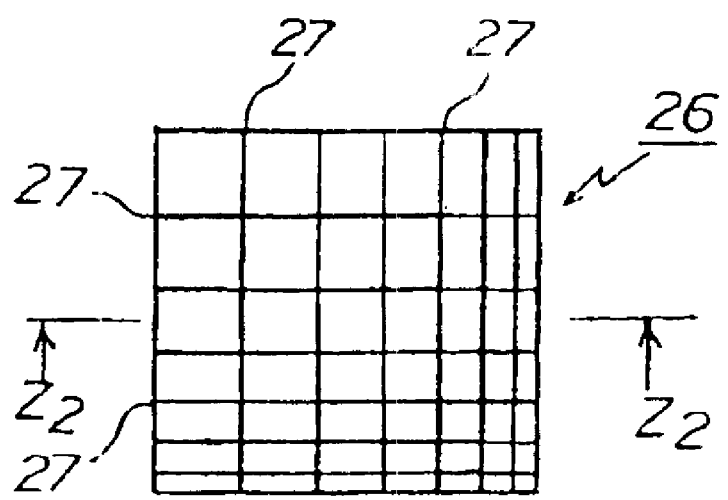
FIG. 12 is a schematic view to conceptually explain a periodic pattern of diffraction grating grooves of a diffraction grating plate shown in FIG. 11.
Figure 13:
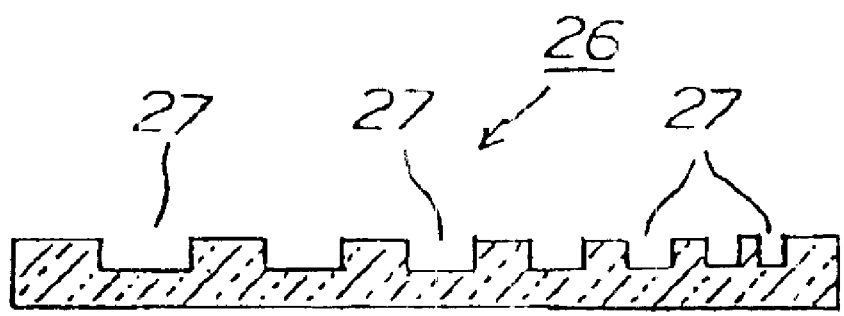
FIG. 13 is a cross-sectional view taken along line Z2—Z2 indicated by arrows of FIG. 12.
Figure 14:
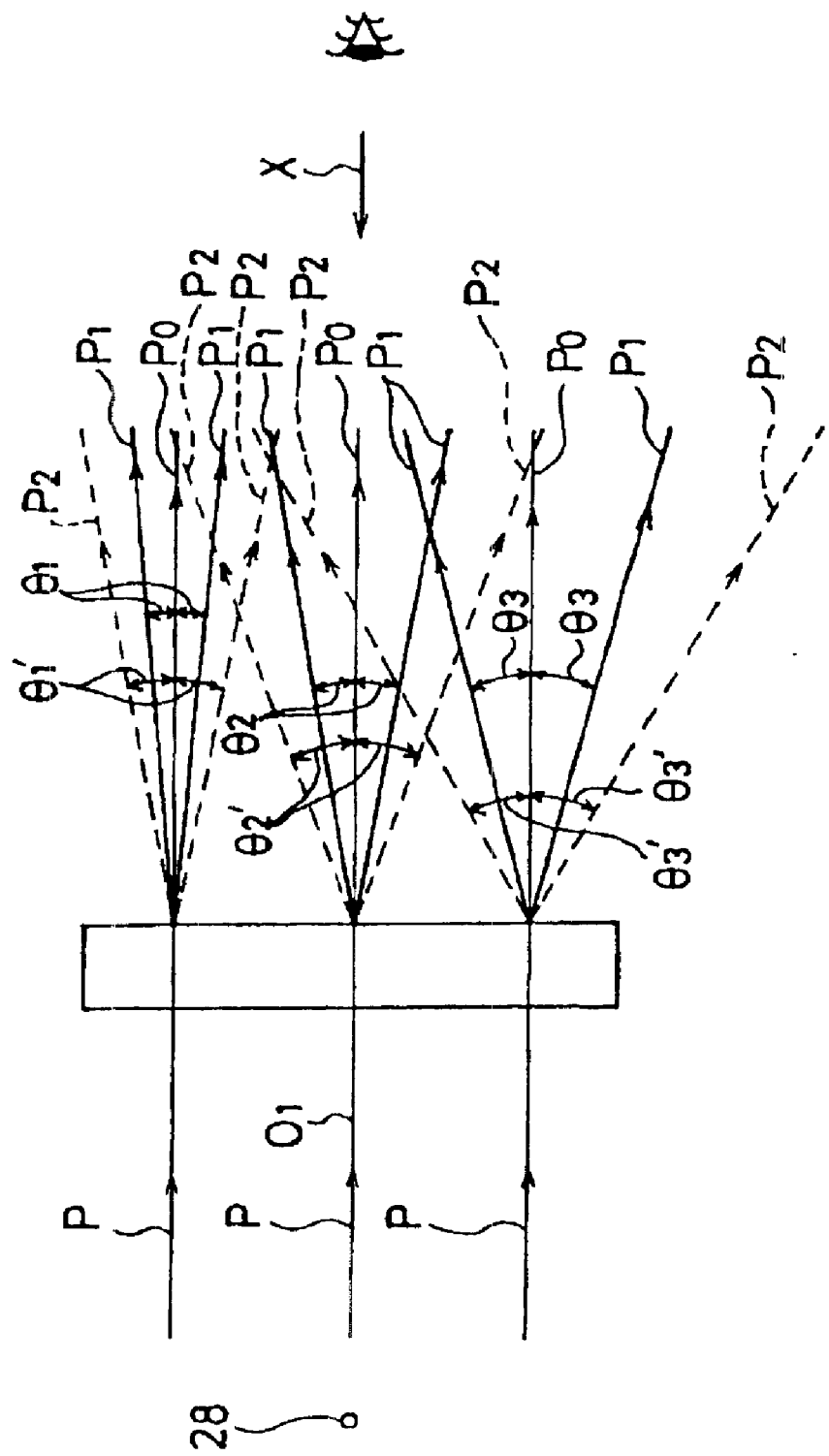
FIG. 14 is an explanatory view to explain the function of the diffraction grating plate shown in FIG. 12.

As schematically shown in FIGS. 12 and 13, in the diffraction grating plate 26, diffraction grating grooves 27 whose periodicity (pitch) continuously changes are formed vertically and horizontally. When a light beam P is incident from a point source 28 with a single color (short wavelength) through the diffraction grating plate 26, a zero-order light P0, first-order diffraction light P1, second-order diffraction light P2, . . . are generated by the respective diffraction gratings as illustrated in FIG. 14.

The zero-order light P0 is light that travels in a straight line through the diffraction grating plate 26, and the first-order diffraction light P1 is light whose direction is bent by first-order diffraction. The second-order diffraction light P2 is light whose direction is bent by first-order diffraction. However, diffraction angles $\theta1, \theta2, \theta3, \ldots$ of the first-order diffraction light P1 increase in order as the width of the diffraction grating groove 27 becomes narrower. Namely, a relationship, $\theta1<\theta2<\theta3<\ldots$, is established. Similarly, diffraction angles $\theta1'<\theta2'<\theta3'<, \ldots$ of second-order diffraction light P2 increase in order as the width of diffraction grating groove 27 becomes narrower. Namely, a relationship, $\theta1'<\theta2'<\theta3'<\ldots$, is established.

Accordingly, if attention is paid to only zero-order diffraction light P0, the light beam, which is based on this zero-order diffraction light P0, corresponds to a spherical lens with degree of 0. If attention is paid to only the first-order diffraction light P1 of the upper side, the first-order diffraction light P1 of the upper side acts on a converging direction, so that the first-order diffraction light P1 functions as an imaginary convex lens with given degrees. Moreover, if attention is paid to only the first-order diffraction light P1 of the lower side, first-order diffraction light P1 of the lower side acts on a diverging direction, so that the first-order diffraction light P1 functions as an imaginary concave lens with given degrees. Still moreover, if attention is paid to only second-order diffraction light P1 of the upper side, the diffraction angles $\theta1'<\theta2'<\theta3'<, \ldots$ increase two times as large as diffraction angles $\theta1<\theta2<\theta3<, \ldots$ of first-order diffraction light P2 of the upper made, so that the second-order diffraction light P2 of the upper side functions as an imaginary convex lens that has degrees, which are two times as large as an imaginary convex lens with given degrees formed by the first-order diffraction light P1 of the upper side. Similarly, the second-order diffraction light P2 of the lower side functions as an imaginary concave lens that has degrees, which are two times as large as an imaginary concave lens with given degrees formed by the first-order diffraction light P1 of the lower side.

Accordingly, a plurality of images, which are based on the plurality of point sources, are seen on a plane orthogonal to an optical axis O1 an at different distances in a direction of optical when seeing the point source 28 with a single color from a direction of an arrow X through the diffraction grating plate 26.

By devising ingenuity to the diffraction grating grooves 27 of the diffraction grating plate 26, it is possible to prepare an optical element that has a function exhibited by combing a concave cylindrical lens whose degree differs 0.25D by 0.25D and whose cylindrical axis O is orthogonal thereto with a convex cylindrical lens.

Figure 15:
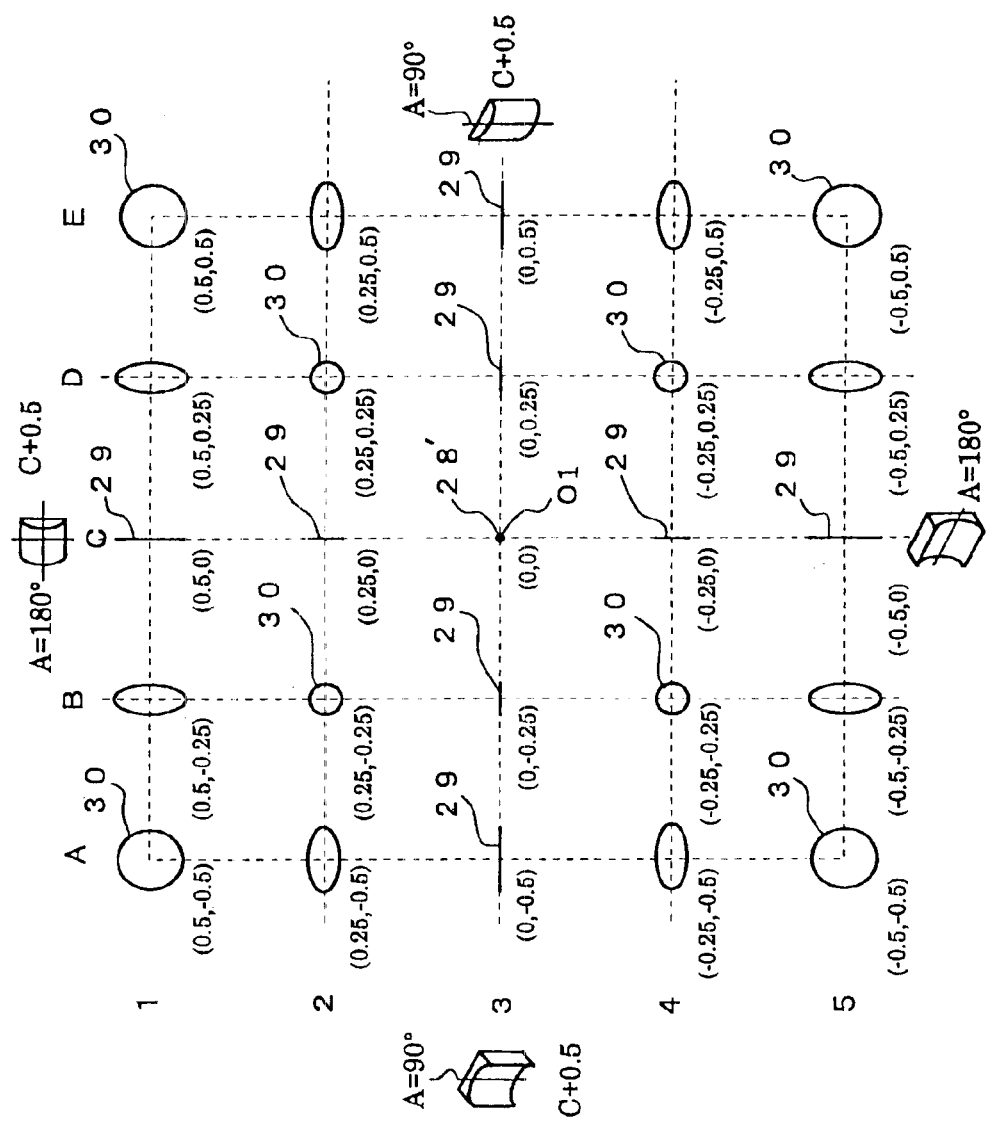
FIG. 15 is an explanatory view illustrating the way how the target is seen when a point source with a single color is seen via the diffraction grating plate shown in FIG. 12.

Specifically, when a person, who has good eyesight or ideally corrected eyesight, sees the point source 28, a radiant image 28' of the point source 28 is seen on the optical axis O1 as illustrated in FIG. 15. In a vertical upper direction, a focal line image 29, which corresponds to a convex cylindrical lens with cylindrical degree C and axial angle A (=180 degrees) of the cylindrical axis O, is seen. In a vertical lower direction, a focal line image 29, which corresponds to a concave cylindrical lens with the cylindrical degree C and the axial angle A (=180 degree) of the cylindrical axis O, is seen. At a horizontally right side, a focal line image 29, which corresponds to a convex cylindrical lens with the axial angle A (=90 degrees) of the cylindrical axis O, is seen. At a horizontally left side, a focal line image 29, which corresponds to a concave cylindrical lens with the cylindrical degree C and axial angle A (=90 degrees) of the cylindrical axis O, is seen. Then, in diagonal direction between the vertical and horizontal directions, a circle of confusion image 30 is seen. In this way, the diffraction grating plate 26 can be prepared.

In view of the diagonal direction, the diameter of the circle of confusion increases gradually from the optical axis O1. In accordance with the degree of the blur of image, if the circle of confusion image 30 exists on the front side in the direction of optical axis O1 and below the optical axis O1, the circle of confusion image 30 exists on the other side of the optical direction and above the optical axis O1.

Figure 16:
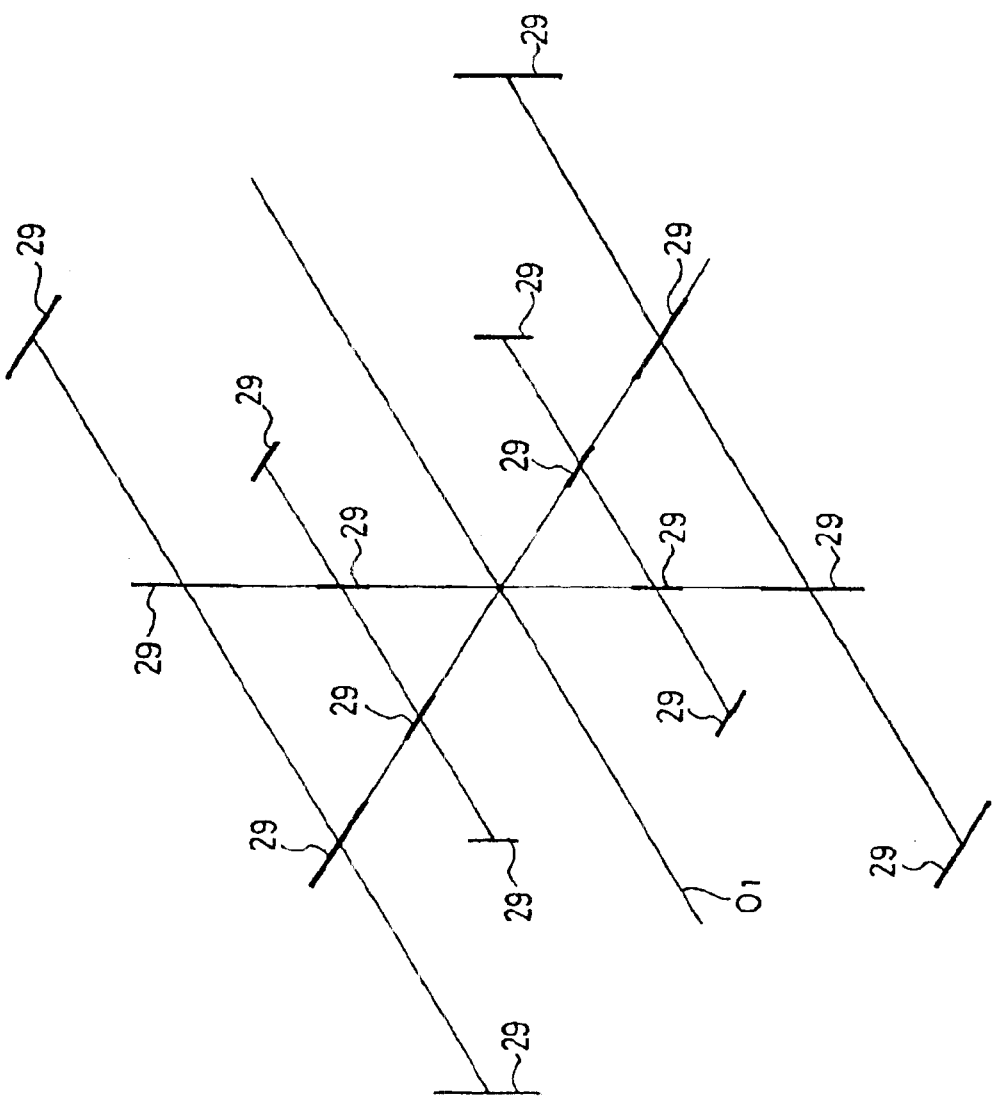
FIG. 16 is an explanatory view illustrating that a focal line image as a target is shown three-dimensionally when a point source with a single color is seen via the diffraction grating plate shown in FIG. 12.

Namely, if only the positions where the focal line images are formed is shown three-dimensionally, they are as illustrated in FIG. 16.

Figure 17:
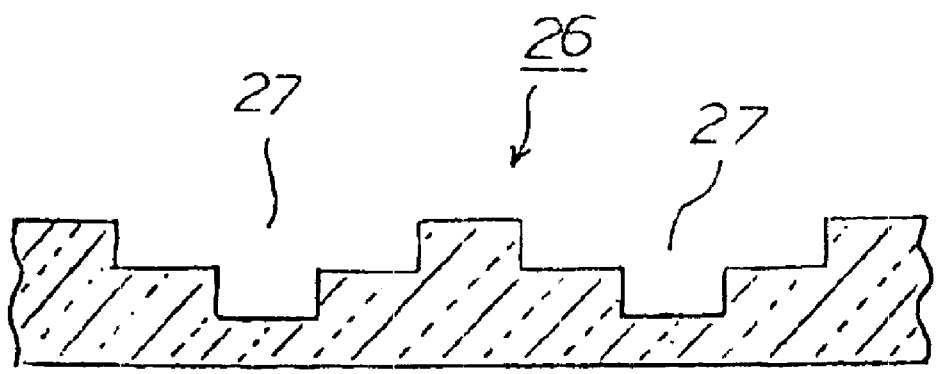
FIG. 17 is a partially enlarged cross-sectional view of diffraction grating grooves to explain a state in which the diffraction grating grooves are formed stepwise to make luminance of each target image constant.

Additionally, by modifying the cross-sectional shape of the diffraction grating groove of diffraction grating plate 26 to a shape as illustrated in an enlarged view of FIG. 17, the image of light source based on the zero-order diffraction light P0, that of light source based on the first-order diffraction light P1 and that of the second-order diffraction light P2 can have substantially the same intensity.

When such diffraction grating plate 26 is inserted in the optical path of a correction optical system 1 as illustrated in FIG. 11, the light source (LED) 28 with a single color (short wavelength) is turned on in synchronization with the insertion of this diffraction grating plate 26. Then, a point target 31a is shown to the eyes E to be subjected to optometry through a pin hole 31a of a pin hole plate 31.

If is point target 31a is seen through the spherical lens 24, cylindrical lens 25, and diffraction grating plate 26 of the correction optical system 1, a plurality of target images are seen as if they were dispersed on a plane orthogonal to the optical axis O1 and shown simultaneously and symmetrically at a different distance in a direction of optical based on the real point target 31a as illustrated in FIG. 11.

Figure 18:
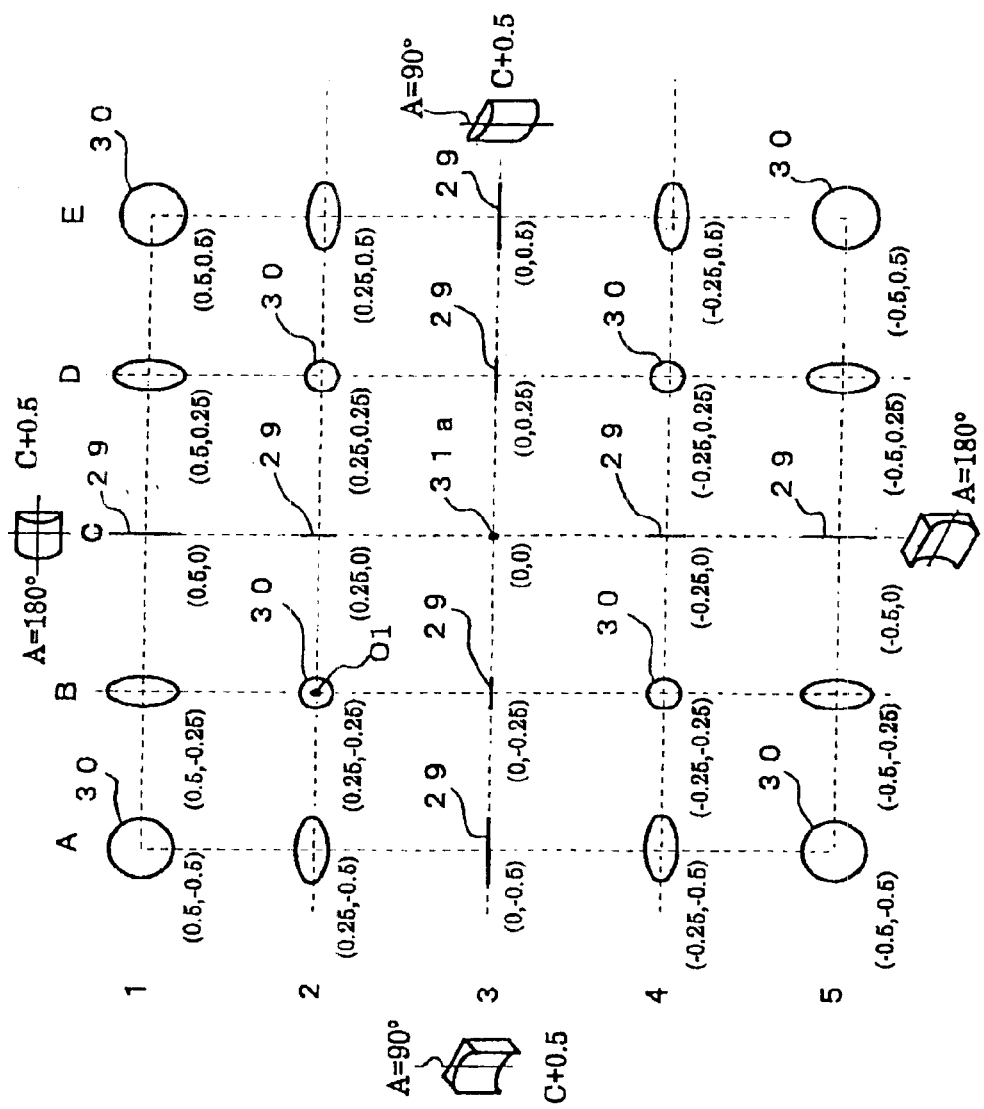
FIG. 18 is an explanatory view to explain a state in which a position of a point target is seen as if it were shifted from the optical axis of correction optical system.
Figure 19:
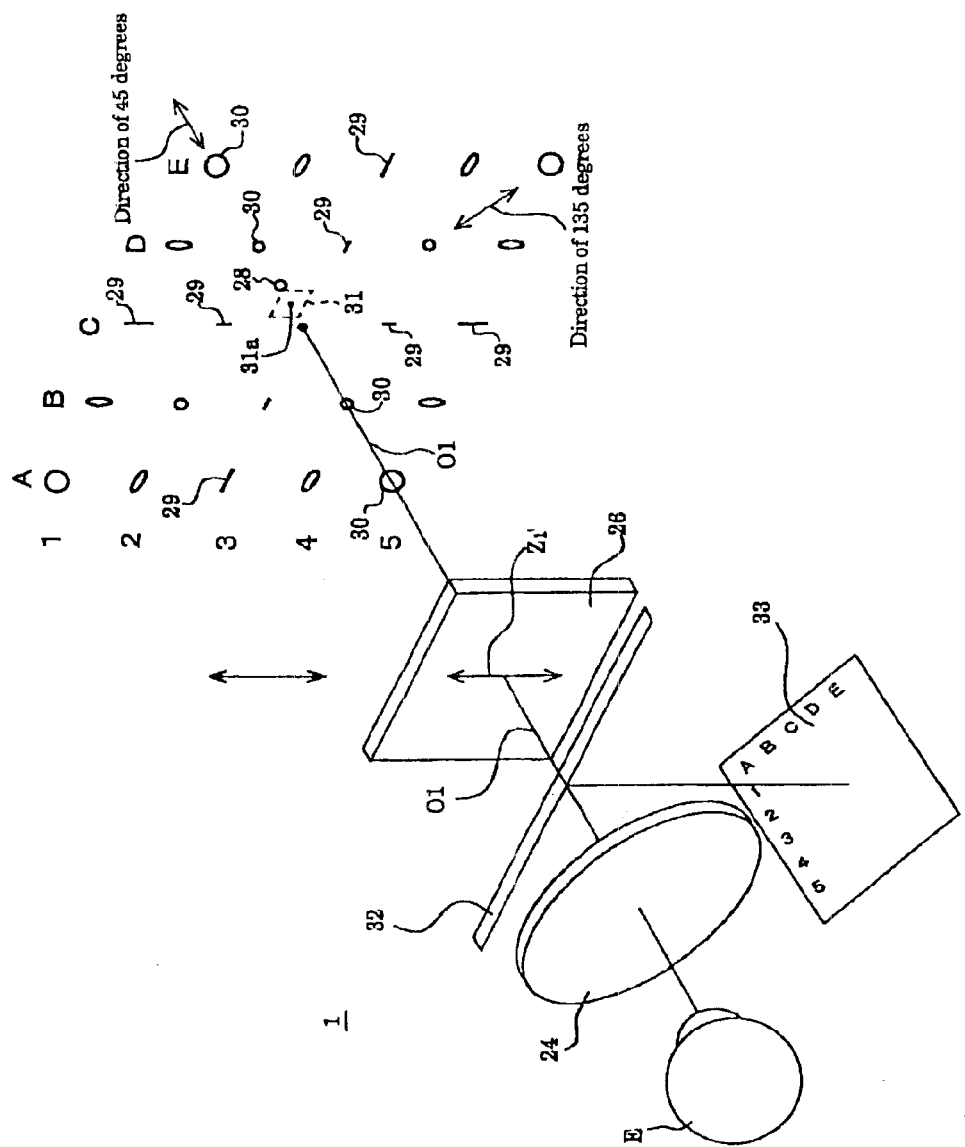
FIG. 19 is a schematic view illustrating one example of the correction optical system to which such ingenuity that a matrix sign table is made to correspond to a target image to be shown to a subject is made.

In a case where correction to the examined eyes E to be subjected to optometry is ideally made, the point target 31a is seen as if it was positioned on the optical axis O1 as shown in FIG. 11. However, in a case where correction to the eyes E to be subjected to optometry is not ideally made, the point target 31a is seen as if it was placed at a position shifted from the optical axis O1 as shown in FIG. 18.

Accordingly, if the correction optical system 1 is adjusted such that the point target 31a is positioned on the optical axis O1, it is possible to carry out precise measurement of the astigmatic axis and astigmatic degree of the subject.

In connection with ingenuity to decide the position of the point target 31a, for example, a hall mirror 32 is diagonally provided at the optical path of the correction optical system 1 so that a matrix sign table 33 including numerals and English letters in rows and columns is reflected in the half mirror 32. Then, the numerals and English letters of the matrix sign table 33 are shown to the eyes E to be subjected to optometry simultaneously so that the position of the point target 31a may be designated using the numerals and English letters.

Additionally, it is possible to adopt a structure in which without providing the half mirror 32, the matrix sign table 33 is directly displayed in the optical path of the correction optical system 1 with a wavelength by which no diffraction power is produced.

Moreover, the horizontal right side corresponds to a convex cylindrical lens with the axial angle A (=90 degrees) of the cylindrical axis O and the cylindrical degrees (C=0.25 and 0.5). The horizontal left side corresponds to the concave cylindrical lens with the axial angle (=90 degrees) A of the cylindrical axis O and the cylindrical degrees C (=−0.25 and −0.5). The vertical upper side corresponds to the convex cylindrical lens with the axial angle A (=180 degrees) of the cylindrical axis O and the cylindrical degrees C (=0.25 and 0.5). The vertical lower side corresponds to the concave cylindrical lens with the axial angle A (=180 degrees) of the cylindrical axis O and the cylindrical degrees C (=−0.25 and −0.5). The diagonal direction corresponds to the change in the degree of the spherical lens. Accordingly, as shown in FIG. 10, such a structure may be adopted that the subject himself or herself operates the joystick 33' to associate the movement of joystick 33' in a slanting direction with the change in the spherical degree S and to see the point target 31a as if it was positioned on the optical axis O1 in accordance with an exchange between convex and concave cylindrical lenses and a change in the cylindrical degree C as leaving the axial angle A of the cylindrical axis 0=90 degrees unchanged so as to correspond to in accordance with the horizontal movement of a joystick 33' of controller 24, as well as in accordance with an exchange between convex and concave cylindrical lenses and a change in the cylindrical degree C as leaving the axial angle A of the cylindrical axis 0=180 degrees unchanged so as to correspond to the vertical movement of joystick 33'.

Figure 20:
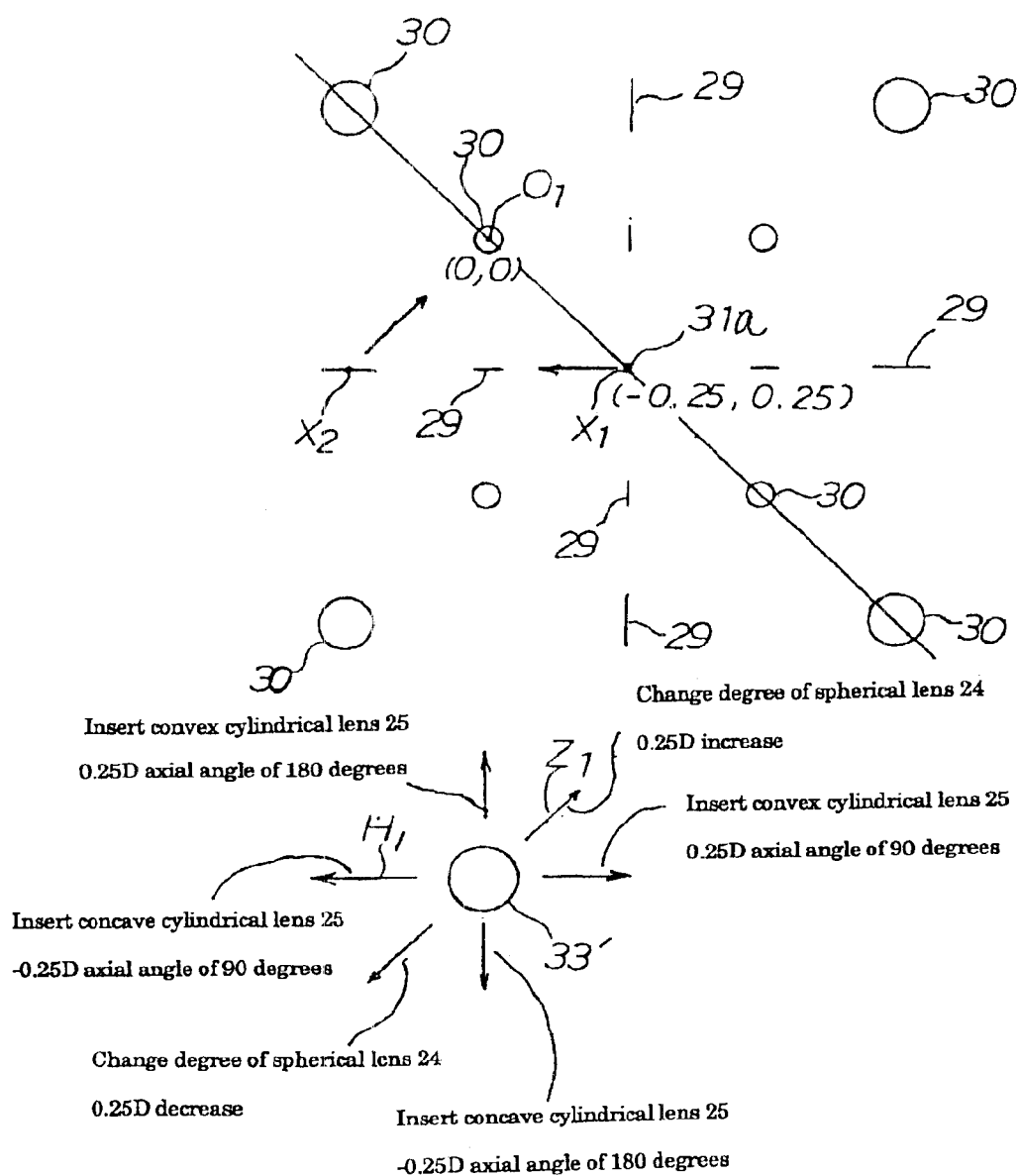
FIG. 20 is an explanatory view illustrating a state in which a subject himself/herself operates a joystick to adjust the position of target image.

For example, when the point target 31a is seen at a position of −0.25D vertically and a position of +0.25D horizontally as illustrated in FIG. 20, the joystick 33' is operated in a left direction (direction of an arrow H1). Resultantly, in syncronization with the operation of joystick 33' in a left direction, the degree of the cylindrical lens 25 to be inserted in the optical path of the correction optical system 1 is changed to −0.25D. When this operation is continued two times, the position of the point target 31a that can be clearly seen is moved from a position X1 to a position X2.

After that, the joystick 33' is operated in a direction of an arrow Z1 to increase the degree of the spherical lens 24 to be inserted in the optical path of correction optical system 1 by 0.25. Resultantly, the position of the point target 31a that can be clearly seen is moved from the position X2 to the optical axis O1.

This makes it possible for the subject himself or herself to carry out precise measurement of the astigmatic axis and astigmatic degree.

In addition, when the diffraction grating plate 26 is inserted in the optical path of the correction optical system 1, the amount of light is reduced by the diffraction function of the diffraction grating plate 26 as compared with the case in which no the diffraction grating plate 26 is inserted. In this case, the amount of light of the point source 28 may be increased by an amount correspond to the reduction of the amount of light.

In connection with precise measurement of the astigmatic axis and astigmatic degree using this diffraction grating plate 26, the following will specifically explain three embodiments.

(Embodiment 1)

First, similar to the conventional case, a spherical degree S, a cylindrical degree C and an axial angle A of the cylindrical axis O are roughly measured by the fogging measurement method.

Next, the diffraction grating plate 26 is inserted in the optical path of the correction optical system 1. The initial setting of the diffraction grating plate 26 to the optical path of the correction optical path 1 is designed such that a direction where one diffraction grating groove 27 extends is a vertical direction. In FIG. 11, an arrow Z1' shows a direction where one diffraction grating groove 27 extends.

In association with the insertion of the diffraction grating plate 26 to the optical path, the point source 28 with a single color is turned on. Then, the subject is caused to pay attention to the diagonal directions (45 degrees, 135 degrees) shown in FIG. 11.

After this, the degree of spherical lens is changed to adjust the point target 31a to be positioned on substantially the optical axis O1. Thus, precise measurement of the spherical degree S is carried out. Next, the direction where the diffraction grating groove 27 of the action grating plate 26 extends is roughly conformed to the direction where the cylindrical axis O extends. Here, the cylindrical axis O is conformed to the direction Z1' where one diffraction grating groove 27 extends.

Then, the diffraction grating plate 26 is slightly rotated with the cylindrical lens 25. Namely, the cylindrical lens 25 and diffraction grating plate 26 are slightly rotated +0.5 and −0.5 degrees about the optical axis with respect to the axial angle A (=90 degrees) of the cylindrical axis O roughly obtained. Thus, precise measurement of the axial angle A of the cylindrical axis O is carried out.

Next, the cylindrical degree C of the cylindrical lens 25 is changed and adjusted by 0.25D such that the length and clearness of the focal line images 29, which intersect at right angles, become symmetric with respect to the point target 31a. This carries out precise measurement of the cylindrical degree C (Embodiment 2)

The approximate measurement of a spherical degree S, a cylindrical degree C and an axial angle A of the cylindrical axis is the same that of Embodiment 1.

The diffraction grating plate 26 is inserted in the correction optical system 1, and the diffraction grating plate 26 is subjected to initial setting so that a direction where one diffraction grating groove 27 extends is a vertical direction. Then, the subject is caused to designate the position where the point target 31a can be seen using the joystick 33' in the initial setting state of the diffraction grating plate 26.

It is possible to designate the position using the matrix sign table 33 in place of the joystick 33'.

A program that associates each position, which is seen as being discrete spatially, with power (which is used as concept including the cylindrical degree, convex and concave) of the cylindrical lens is installed onto the controller 24.

The controller 24 has a program that computes the spherical degree S of the position where the point target can be seen, the cylindrical degree C and axial angle A of cylindrical axis O based on power of the cylindrical lens in the vertical direction, which corresponds to the position where the subject can see the point target 31a, and power of the cylindrical lens in the horizontal direction.

In connection with the spherical degree S, cylindrical degree C and axial angle A, for example, the following equations are used.

The following will explain general equations of a cross cylindrical lens and a toric lens.

The cross cylindrical lens is obtained when axes of two cylindrical lenses, each having a different sign and the same refractive power, are orthogonal to each other and combined. This can be expressed as a combination of a spherical lens and a cylindrical lens, and can be represented by the same equation as used in the toric lens.

Now, it is assumed that a spherical degree of the toric lens is S, a cylindrical degree is C, and an axial angle is A. Refractive power $D\theta$ in a longitudinal direction at position with an angle $\theta$ from the cylindrical axis O can be expressed as follows:

$$D\theta = S + C \sin^2(\theta - A)$$

This general equation can be deformed as follows:

$$D\theta = (S + C/2) - (C/2)\cos 2(\theta - A)$$

$$D\theta = (S + C/2) - (C/2)(\cos 2\theta \cos 2A + \sin 2\theta \sin 2A) \quad (a)$$

The composite equation of two toric lenses is obtained as follows:

In connection with the toric lens with composite refractive power $D\theta_0$ obtained by combining two toric lenses each having refractive power $D\theta_1$ and $D\theta_2$, if each spherical degree, cylindrical degree and axial angle are $D\theta_1$ ($S_1$, $C_1$, $A_1$), $D\theta_2$ ($S_2$, $C_2$, $A_2$), and $D\theta_0$ ($S_0$, $C_0$, $A_0$) respectively, each toric lens can be expressed as follows from equation (a):

$$D\theta_1 = (S_1 + C_1/2) - C_1/2(\cos 2\theta \cos 2A_1 + \sin 2\theta \sin 2A_1)$$

$$D\theta_2 = (S_2 + C_2/2) - C_2/2(\cos 2\theta \cos 2A_2 + \sin 2\theta \sin 2A_2)$$

$$D\theta_0 = (S_0 + C_0/2) - C_0/2(\cos 2\theta \cos 2A_0 + \sin 2\theta \sin 2A_0) \quad (b)$$

Werein, since $D\theta_0$ is the sum of $D\theta_1$ and $D\theta_2$, the following equation is given:

$$D\theta_0 = (S_1 + S_2 + (C_1 + C_2)/2) - C_1/2(\cos 2\theta \cos 2A_1 + \sin 2\theta \sin 2A_1) - C_2/2(\cos 2\theta \cos 2A_2 + \sin 2\theta \sin 2A_2)$$

If the above equation is deformed, the following equation is given:

$$D\theta_0 = (S_1 + S_2 + (C_1 + C_2)/2) - (C_1/2 \cos 2A_1 + C_2/2 \cos 2A_2)\cos 2\theta - ((C_1/2)\sin 2A_1 + (C_2/2)\sin 2A_2)\sin 2\theta \quad (c)$$

From the correspondence between equations (b) and (c), the following equations can be obtained:

$$(S_0 + C_0/2) = (S_1 + S_2 + (C_1 + C_2)/2) \quad (d)$$

$$C_0 \cos 2A_0 = C_1 \cos 2A_1 + C_2 \cos 2A_2 \quad (e)$$

$$C_0 \sin 2A_0 = C_1 \sin 2A_1 + C_2 \sin 2A_2 \quad (f)$$

Equation (d) can be written as follows:

$$S_0 = (S_1 + S_2 + (C_1 + C_2)/2) - C_0/2 \quad (g)$$

If both sides of equations (e) and (f) are squared to find the sum, the following equation is obtained:

$$C_0 = \pm\sqrt{(C_1^2 + C_2^2 + 2C_1 C_2 \cos 2(A_1 - A_2))} \quad (h)$$

From the product of (e) and (f), the following equation is given:

$$A_0 = (1/2)\tan^{-1}(C_1 \sin 2A_1 + C_2 \sin 2A_2)/(C_1 \cos 2A_1 + C_2 \cos 2A_2) \quad (i)$$

Here, the value of $A_0$ follows the following relationship when $C_1 \sin 2A_1 + C_2 \sin 2A_2 = Y$ and $C_1 \cos 2A_1 + C_2 \cos 2A_2 = X$.

When X=0 AND Y=0, $A_0 = 0°$

When X=0 AND Y>0, $A_0 = 45°$

When X=0 AND Y<0, $A_0 = 135°$

When Y=0 AND X>0, $A_0 = 0°$

When Y=0 AND X<0, $A_0 = 90°$

When X>0 AND Y>0, $A_0 = A°$

When X<0 AND Y>0, $A_0 = A° + 90°$

When X<0 AND Y<0, $A_0 = A° + 90°$

When X>0 AND Y<0, $A_0 = A° + 180°$

Thus, the spherical degree $S_0$, cylindrical degree $C_0$ and axial angle $A_0$ of cylindrical axis O of the composite refractive power $D\theta_0$ obtained by combining two toric lenses can be obtained from equations (g) to (i).

Sequentially, the composite spherical degree $S_0$, cylindrical degree $C_0$, and axial angle $A_0$ are calculated based on the spherical degree $S_0$, cylindrical degree $C_0$ and axial angle $A_0$ thus obtained and the spherical degree s, cylindrical degree C and axial angle A obtained by the approximate measurement.

Then, the spherical lens 24 and cylindrical lens 25, which correspond to the composite spherical degree $S_0$, cylindrical degree $C_0$, and axial angle $A_0$, are set to the correction optical system 1. At this time, the axial angle $A_0$ of cylindrical lens 25 is also conformed to the composite axial angle A.

Then, the diffraction grating plate 26 is rotated about optical axis O1 by 45 degrees, and the subject is caused to designate the position where the point target 31a can be seen using the joystick 33' in a like manner.

At the position where this diffraction grating plate 26 is rotated by 45 degrees, the spherical degree S, cylindrical degree C, and axial angle A of cylindrical axis O at the position where the point subject 31a can be seen are obtained by calculation. Then, the composite spherical degree S, cylindrical degree C and axial angle A of cylindrical axis O including the spherical degree S, cylindrical degree C, and axial angle A of cylindrical axis O obtained by this calculation and the spherical degree S, cylindrical degree C and axial angle of cylindrical axis O obtained by the approximate measurement are obtained.

The composite spherical degree S, cylindrical degree C and axial angle A of cylindrical axis O are obtained, so that precise measurement is ended.

(Embodiment 3)

Figure 21:
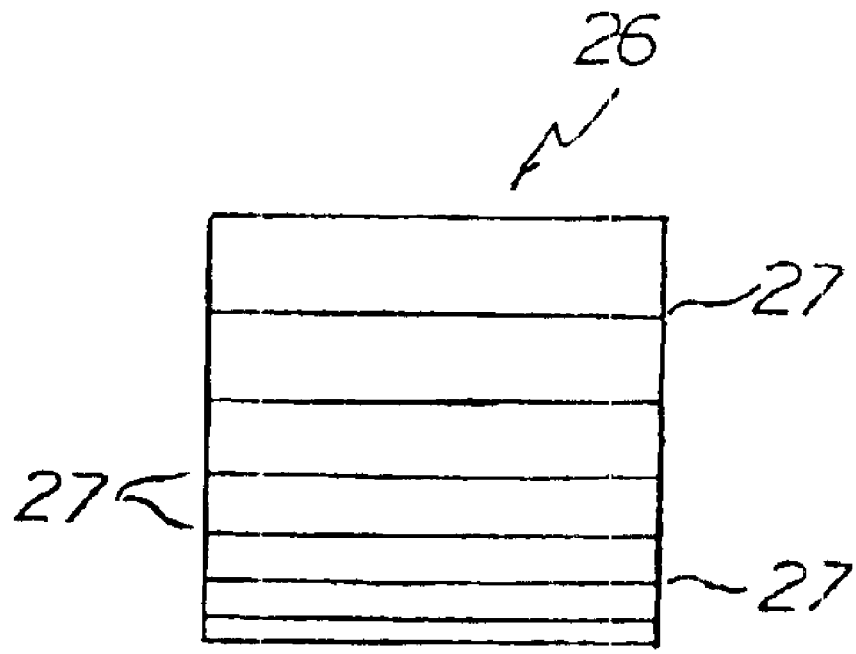
FIG. 21 is a schematic view conceptually showing other example of a periodic pattern of the diffraction grating grooves of the diffraction grating plate.
Figure 22:
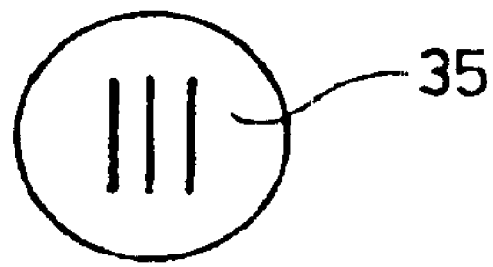
FIG. 22 is an explanatory view illustrating other example of a target to be shown via the diffraction grating plate of FIG. 21.
Figure 23:
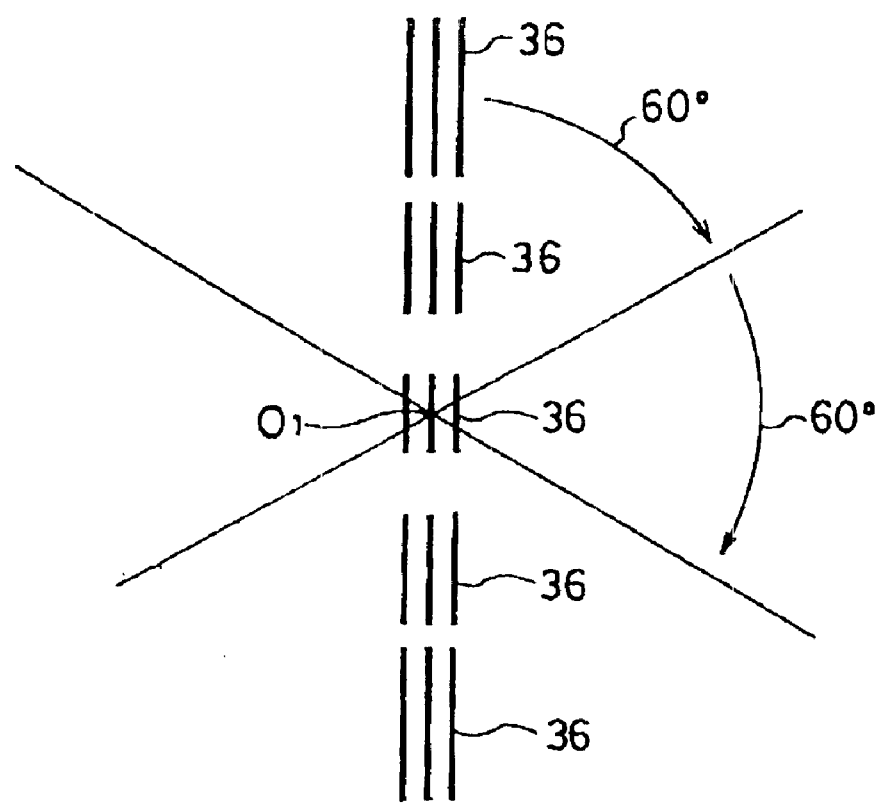
FIG. 23 is an explanatory view illustrating one example of the way how the target is seen when the target of FIG. 22 is seen via the diffraction grating plate of FIG. 21.

In the case of Embodiment 3, as illustrated in FIG. 21, the diffraction grating plate 26 having only the diffraction grating groove 27, which extends longer horizontally, is used. Moreover, as illustrated in FIG. 22, a target 35 with three lines, which extend longer vertically, is used. This target 35 is illuminated by the light source 28 with a single color.

When the target 35 is seen through the diffraction grating plate 26 shown in FIG. 21, a plurality of target images 36 (five) can be seen. At this time, if eyesight of the eyes E to be subjected to optometry is normal or subjected to correction ideally, that is, the astigmatic axis is adjusted and eyesight is normal, the length of the target image 36 on the optical axis O1 is seen in a state that the length is short and the lines in the vertical direction are uniformly seen clearly.

When the degree of eyes to be subjected to optometry is not adjusted, the length of the target image 36, which is placed at the position shifted from the optical axis O1, is the shortest and the image can be clearly seen. Other target images 36 are seen blurrily.

Here, in the initial state, the direction where the diffraction grating groove 27 of diffraction grating plate 26 is set to the horizontal direction, the position of target image 36, which is clearly seen as compared with the other target images 36, is designated using the joystick 33'.

Similar to Embodiment 2, the spherical degree S, cylindrical degree C, and axial angle A of cylindrical axis O are obtained based on the above. Then, the composite spherical degree S, cylindrical degree C and axial angle A of cylindrical axis O are calculated based on the spherical degree S, cylindrical degree C, and axial angle A of cylindrical axis O obtained by the calculation and the spherical degree S, cylindrical degree C and axial angle of cylindrical axis O obtained by the approximate measurement.

The spherical lens 24 and cylindrical lens 25, which correspond to the composite spherical degree S, cylindrical degree C, and axial angle A of cylindrical axis O, are set to the correction optical system 1. At this time, the axial angle A of cylindrical axis O of cylindrical lens 25 is also conformed to the composite axial angle A.

Then, the diffraction grating plate 26 is rotated about the optical axis O1 by 60 degrees, and the subject is caused to designate the position of target image 36, which is clearly seen as compared with the other target images 36, using the joystick 33', again.

By the similar calculation, the composite spherical degree S, cylindrical degree C and axial angle A of cylindrical axis O are calculated. Then, the spherical lens and cylindrical lens, which correspond to the composite spherical degree S, cylindrical degree C, and axial angle A of cylindrical axis O are set to the correction optical system 1. Then, the diffraction grating plate 26 is rotated about the optical axis O1 by 60 degrees, again.

Then, the subject is caused to designate the position of target image 36, which is clearly seen as compared with the other target images 36, using the joystick 33', again.

By the similar calculation, the composite spherical degree S, cylindrical degree C and axial angle A of cylindrical axis O are calculated, again.

Thus, measurement in a longitudinal direction is performed to the eyes E to be subjected to optometry, and precise measurement of astigmatic degree and astigmatic axis of the eyes E to be subjected to optometry is ended.

According to the present invention, it is possible to precisely measure the spherical degree, angle of astigmatic degree, and astigmatic degree at one time. Moreover, it is possible to make the correction optical system of optometry compact.

What is claimed is:

1. An optometry apparatus comprising:
   an optical element constructed so that targets appear to examined eyes to be subjected to optometry as if the targets were dispersed on a plane orthogonal to an optical axis and shown simultaneously at different positions in the direction of the optical axis,
   wherein said optical element is a diffraction grating plate including diffraction grating grooves whose pitches are different.

2. An optometry apparatus comprising:
   an optical element provided in a correction optical system which has a spherical lens and a cylindrical lens for correction of eyes of a subject, said optical element being constructed such that a plurality of targets appears to the eyes as if the targets were dispersed in a plane orthogonal to an optical axis and shown simultaneously at different positions in the direction of the optical axis,
   wherein said optical element is a diffraction grating plate including diffraction grating grooves whose pitches are different.

3. A diffraction grating plate including diffraction grating grooves whose pitches are different constructed such that targets appear to eyes to be as if the targets were dispersed in a plane orthogonal to an optical axis and shown simultaneously at a different position in a direction of an optical axis through eyes to be subjected to optometry.

4. The optometry apparatus according to claim 3, wherein said optical element is capable of movement along an optical path of said correction optical system.

5. The optometry apparatus according to claim 2, wherein when said diffraction grating plate is inserted in an optical axis of said correction optical system, the targets are shown by a single-color light source.

6. The optometry apparatus according to claim 4, wherein when said diffraction grating plate is inserted in an optical axis of said correction optical system, the targets are shown by a single-color light source.

7. The optometry apparatus according to claim 5, wherein when said diffraction grating plate is inserted in the optical axis of said correction optical system, a light quantity of the single-color light source is increased.

8. The optometry apparatus according to claim 6, wherein when said diffraction grating plate is inserted in the optical axis of said correction optical system, a light quantity of the single-color light source is increased.

9. The optometry apparatus according to claim 2, wherein a subject designates a target, which seems to be the best among the plurality of targets shown simultaneously and adjusts said correction optical system.

10. The optometry apparatus according to claim 9, wherein matrix signs, which can designate said plurality of targets in the form of matrix, are simultaneously shown to the eyes to be subjected to optometry such that the subject is caused to designate the target, which seems to be the best among the plurality of targets shown simultaneously.

11. The optometry apparatus according to claim 10, wherein said matrix signs are shown in an optical path of said correction optical system through a half mirror.

12. The optometry apparatus according to claim 10, wherein said matrix signs are shown with a wavelength by which no diffraction power is generated.

13. The optometry apparatus according to claim 2, wherein the subject adjusts said correction optical system using a joystick, designating a target which seems to be the best among the plurality of targets shown simultaneously.

14. The optometry apparatus according to claim 2, wherein said diffraction grating plate is rotated together with the cylindrical lens, so that a spherical degree, a cylindrical degree and an axial angle of a cylindrical axis are precisely measured.

15. The optometry apparatus according to claim 2, wherein said diffraction grating plate is rotated by 45 degrees from an initial setting state, a spherical degree, a cylindrical degree and an axial angle of a cylindrical axis are determined by calculation, and a spherical degree, a cylindrical degree and an axial angle of a cylindrical axis are determined by calculation where the spherical degree, the cylindrical degree and the axial angle of cylindrical axis determined by the calculation are synthesized with a cylindrical degree and an axial angle of a cylindrical axis determined by approximate measurement, and the spherical degree, the cylindrical degree and the axial angle of cylindrical axis are precisely measured by the synthesized spherical degree, cylindrical degree, and axial angle of cylindrical axis obtained by this calculation.

16. The optometry apparatus according to claim 2, wherein said diffraction grating plate is rotated by 60 degrees two times from an initial setting state, a spherical degree, a cylindrical degree and an axial angle of a cylindrical axis are determined by calculation, and a spherical degree, a cylindrical degree and an axial angle of a cylindrical axis are determined by calculation where the spherical degree, the cylindrical degree and the axial angle of cylindrical axis determined by the calculation are synthesized with a spherical degree, a cylindrical degree and an axial angle of a cylindrical axis determined by approximate measurement, and the spherical degree, the cylindrical degree and the axial angle of cylindrical axis are precisely measured by the synthesized spherical degree, cylindrical degree and axial angle of cylindrical axis determined by this calculation.

* * * * *